US006514919B2

(12) United States Patent
Lambino et al.

(10) Patent No.: US 6,514,919 B2
(45) Date of Patent: Feb. 4, 2003

(54) CLEAR CLEANSING BAR COMPOSITIONS THAT ARE EFFICIENT AND ARE NOT IRRITATING TO THE EYES

(75) Inventors: Danilo L. Lambino, Kogarah (AU); Annabelle J. Personeni, Monterey (AU); Noble J. Mathew, Killara (AU)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 09/742,922

(22) Filed: Dec. 21, 2000

(65) Prior Publication Data

US 2002/0128163 A1 Sep. 12, 2002

(51) Int. Cl.[7] .................................................. A61K 7/50

(52) U.S. Cl. ....................... 510/141; 510/147; 510/152; 510/153; 510/155

(58) Field of Search ................................. 510/141, 147, 510/152, 153, 155

(56) References Cited

U.S. PATENT DOCUMENTS

| | | | | | |
|---|---|---|---|---|---|
| 4,439,355 | A | * | 3/1984 | Kenkare | 252/541 |
| 5,286,755 | A | | 2/1994 | Kauffmann et al. | |
| 5,703,025 | A | | 12/1997 | Zyngier et al. | |
| 5,919,744 | A | | 7/1999 | Lazarowitz | |
| 5,981,452 | A | * | 11/1999 | Schrader et al. | 510/155 |
| 6,297,205 | B1 | * | 10/2001 | Saxena et al. | 510/141 |

FOREIGN PATENT DOCUMENTS

| | | |
|---|---|---|
| WO | WO 98/14559 A1 | 4/1998 |
| WO | WO 01/23517 A1 | 4/2001 |

* cited by examiner

*Primary Examiner*—Necholus Ogden

(57) ABSTRACT

Cleansing bar compositions that are efficient and have excellent foam properties and low ocular and skin irritation are disclosed. The compositions include dibenzylidene sorbitol as a gelling agent, a glycol solvent, and a combination of anionic, amphoteric, and nonionic surfactants to provide detergency. The compositions may contain hydroxypropyl cellulose as a solidifying synergist.

12 Claims, No Drawings

CLEAR CLEANSING BAR COMPOSITIONS THAT ARE EFFICIENT AND ARE NOT IRRITATING TO THE EYES

BACKGROUND OF THE INVENTION

1. Field of the Invention

This invention relates to cleansing bar compositions, which are clear and exhibit exceptionally low ocular and skin irritation. The cleansing bar compositions have good foaming properties.

2. Description Of The Prior Art

Conventional soap bars are opaque and have several problems associated with them. One problem associated with soap bars is that they tend to absorb water on the surface of the bar and form a gel or mush on the wet surfaces. The gel or mush tends to rinse off the bar upon use and go down the bath or sink drain, resulting in a less efficient soap bar.

Another problem associated with soap bars is that cracks form in the soap bars upon drying after use. The cracks lead to part of the soap bar falling off, usually going down the bath or sink drain, and ultimately a less efficient soap bar.

Many people also find conventional soap bar compositions to be irritating to their eyes. Therefore, there is a need for a cleansing bar that does not form gel or mush, does not crack upon drying, and is not irritating to the eyes.

U.S. Pat. No. 5,286,755 discloses a non-alcoholic cosmetic gel comprising a polyol, a dibenzylidene-ose, a sulfosuccinate hardening agent, and water. The compositions may contain surfactants conventionally employed in cosmetics. The reference does not address the issue of eye irritation and is silent as to suitable genus and species of surfactants for cleansing bar applications.

Despite the disclosure of the prior art, there is a continuing need for a cleansing bar that does not form gel or mush, does not crack upon drying, and is not irritating to the eyes.

It is therefore, the object of the present invention to provide a cleansing bar that does not form gel or mush, does not crack upon drying, and is not irritating to the eyes.

SUMMARY OF THE INVENTION

The present invention provides a clear cleansing bar composition including: a) from about 0.5% to about 30% of at least one amphoteric surfactant; b) from about 0.5% to about 30% of at least one anionic surfactant; c) from about 0.5% to about 30% of at least one non-ionic surfactant; d) from about 0. 1% to about 20% of a solidifying agent; and e) from about 10% to about 90% of at least one organic solvent; wherein the composition is not irritating to the eyes.

DETAILED DESCRIPTION OF PREFERRED EMBODIMENTS

The compositions of the present invention contain at least one amphoteric surfactant. As used herein, the term "amphoteric" means: 1) molecules that contain both acidic and basic sites such as, for example, an amino acid containing both amino (basic) and acid (e.g., carboxylic acid, acidic) functional groups; or 2) zwitterionic molecules which possess both positive and negative charges within the same molecule. The charges of the latter may be either dependent on or independent of the pH of the composition. Examples of zwitterionic materials include, but are not limited to, alkyl betaines and amidoalkyl betaines. The amphoteric surfactants are disclosed herein without a counter ion. One skilled in the art would readily recognize that under the pH conditions of the compositions of the present invention, the amphoteric surfactants are either electrically neutral by virtue of having balancing positive and negative charges, or they have counter ions such as alkali metal, alkaline earth, or ammonium counter ions.

Commercially available amphoteric surfactants suitable for use in the present invention include, but are not limited to amphocarboxylates, alkyl betaines, amidoalkyl betaines, amidoalkyl sultaines, amphophosphates, phosphobetaines, pyrophosphobetaines, carboxyalkyl alkyl polyamines, and mixtures thereof. Cocamidopropylbetaine, lauroamphoglycinate, lauric-myristic phosphobetaines, and lauryl betaine are preferred. The amount of amphoteric surfactant may range from about 0.5% to about 30%, preferably from about 1% to about 20% by weight of the total composition.

The compositions of the present invention also contain at least one anionic surfactant. Suitable anionic surfactants include, but are not limited to alkyl sulfates; alkyl ether sulfates; alkyl monoglyceryl ether sulfates; alkyl monoglyceride sulfates; alkyl monoglyceride sulfonates; alkyl sulfonates; alkylaryl sulfonates; alkyl sulfosuccinates; alkyl ether sulfosuccinates; alkyl sulfosuccinamates; alkyl amidosulfosuccinates; alkyl carboxylates; alkyl amidoethercarboxylates; alkyl succinates; fatty acyl sarcosinates; fatty acyl amino acids; fatty acyl taurates; fatty alkyl sulfoacetates; alkyl phosphates; and mixtures thereof, wherein the alkyl group has from about 10 to about 16 carbon atoms. Preferred anionic surfactants include sodium laureth sulfate and sodium laureth-13 carboxylates. The amount of anionic surfactant may range from about 0.5% to about 30%, preferably from about 1% to about 20% by weight of the total composition.

Nonionic surfactants are also utilized in the compositions of the present invention. One class of nonionic surfactants useful in the present invention are polyoxyethylene derivatives of polyol esters, wherein the polyoxyethylene derivative of polyol ester (1) is derived from (a) a fatty acid containing from about 8 to about 22, and preferably from about 10 to about 14 carbon atoms, and (b) a polyol selected from sorbitol, sorbitan, glucose, $\alpha$-methyl glucoside, polyglucose having an average of about 1 to about 3 glucose residues per molecule, glycerine, pentaerythritol and mixtures thereof, (2) contains an average of from about 10 to about 120, and preferably about 20 to about 80 oxyethylene units; and (3) has an average of about 1 to about 3 fatty acid residues per mole of polyoxyethylene derivative of polyol ester.

Examples of preferred polyoxyethylene derivatives of polyol esters include, but are not limited to PEG-80 sorbitan laurate and Polysorbate 20. PEG-80 sorbitan laurate, which is a sorbitan monoester of lauric acid ethoxylated with an average of about 80 moles of ethylene oxide, is available commercially from ICI Surfactants of Wilmington, Delaware under the tradename, "Atlas G-4280." Polysorbate 20, which is the laurate monoester of a mixture of sorbitol and sorbitol anhydrides condensed with approximately 20 moles of ethylene oxide, is available commercially from ICI Surfactants of Wilmington, Delaware under the tradename "Tween 20."

Another class of suitable nonionic surfactants includes long chain alkyl glucosides or polyglucosides, which are the condensation products of (a) a long chain alcohol containing from about 6 to about 22, and preferably from about 8 to about 14 carbon atoms, with (b) glucose or a glucose-containing polymer. The alkyl glucosides have about 1 to about 6 glucose residues per molecule of alkyl glucoside. The preferred nonionic surfactants include Polysorbate 20 and Polyoxyethylene-Sorbitan Laurate. The amount of non-ionic surfactant may range from about 0.5% to about 30%, preferably from about 1% to about 20% by weight of the total composition.

The compositions of the invention may include a cationic surfactant. Useful cationic surfactants include N-alkyl betaines, quaternary ammonium compounds, amido-amines, N-alkylamines, N-alkylamine oxides, amido-amine betaines, amido-amine salts, amido-amine oxides, sultaines and ethoxylated amines. The amount of cationic surfactant may range from about 0.1% to about 10% by weight of the total composition.

The present invention requires a solidifying agent in order to make soap bars. The solidifying agent may be selected from the group consisting of dibenzylidene alditols (such as sorbitol, xylitol, ribitol), and mixtures thereof. The solidifying agent is present in the cleansing bar at a concentration of from about 0.1% to about 20%, preferably from about 0.5% to about 5% by weight of the total composition.

At least one organic solvent is utilized in the compositions of the present invention. Suitable organic solvents include, but are not limited to dihydroxy aliphatic alcohols containing from 3 to 6 carbon atoms, such as 1,3 propylene glycol, 1,3-butylene glycol, 1,4 butylene glycol and hexylene glycol; polyethylene and polypropylene glycols, such as dipropylene glycol, tripropylene glycol, tetrapropylene glycol and 1,3-propanediol; monohydric alcohols, such as ethanol and propanol; polyhydric alcohols, such as glycerol, diglycerol, and polyglycerol; and mixtures thereof. Preferably, the organic solvent is a mixture of dihydroxy and polyhydric alcohols. The amount of organic solvent may range from about 10% to about 90%, preferably from about 20% to about 80% by weight of the total composition.

The compositions of the present invention optionally contain a solidifying synergist. The solidifying synergist aids the solidifying agent in forming a solid soap bar. Suitable solidifying synergists include, but are not limited to cellulose and guar derivatives, including but not limited to hydroxypropylcellulose, acrylic acid polymers, polyacrylamides, alkylene/alkylene oxide polymers, smectite hydrophilic and organoclays, hydrated and fumed silicas, gelatin, keratin, xanthan and guar gums, carrageenan, agar and alginates. When utilized, the amount of solidifying synergist utilized may range from about 0.05% to about 10%, preferably from about 0.1% to about 5% by weight of the total composition.

Optional ingredients may be incorporated into the composition of this invention. These ingredients include perfumes, colorants and dyes, beads, antimicrobial agents, and insect repellent agents.

The clear soap bar compositions according to the invention may be prepared by means known in the art. In a preferred embodiment, the soap bars are prepared by mixing and heating at least one organic solvent as described above to about 70° C. to about 130° C., when utitilized, the solidifying synergist described above is added and mixing is continued until a clear mucillage is formed. The solidifying agent described above is then added and mixed until fully dissolved. To this mixture is added surfactant(s) and mixed. Optional ingredients like perfume and colorants are added when temperature reaches below about 90° C. The molten stock is then poured into suitable molds of different forms made of plastic or rubber and allowed to cool and harden at ambient conditions. The soap bar compositions may be aerated such that the soap bar will float in water. The clear soap bar may be formed around a small toy.

EXAMPLES

The following examples will more fully illustrate the embodiments of this invention. All parts, percentages and proportions referred to herein are by weight unless otherwise indicated. The examples are provided for illustrative purposes and should not be construed as limiting the scope of the invention.

The sources for the materials utilized in the following examples were as follows: dibenzylidene sorbitol (Disorbene LC) was obtained from Roquette;

hydroxypropyl cellulose (Klucel LFF) from Aqualon Chemicals; gylcerin from Henkel; propylene glycol from Dow Chemicals; sodium laureth-13 carboxylate (Miranate LEC) from Rhodia; cocamidopropyl betaine (Tegobetaine L7) from Goldschmidt; lauric immidazoline betaine (Empigen CDL 30/J) from Albright & Wilson; POE-80 sorbitan monolaurate (Atlas G4280) from Uniqema; and sodium laureth sulfate (EMPICOL ESC 70-AU) from Albright & Wilson.

Example 1

Preparation of a clear Cleansing Bar

A clear cleansing bar composition was prepared by charging 202.5g glycerin and 500g propylene glycol into a 1 kg vessel. The solvents were mixed and heated to 70° C. to 80° C. Hydroxypropylcellulose (2.1 g) was sprinkled into the batch until a clear mucillage was formed. The temperature was then ramped-up to 100–110° C.

Then 20.1 g dibenzylidene sorbitol was added. As soon as the dibenzylidene sorbitol was fully dissolved, the following surfactants were added until a homogeneously clear liquid was formed:

| | |
|---|---|
| sodium laureth sulfate | 38.6 g |
| sodium laureth-13 carboxylate | 4.5 g |
| POE-sorbitan laurate | 63.0 g |
| cocamidopropylbetaine | 125.0 g |
| lauroamphoglycinate | 20.8 g |

Other minor ingredients such as perfume and colorants were added. The batch was cooled to about 80° C. and then poured in a plastic mould which was resistant to 80° C. hot pour temperature. The cleansing bar stock was allowed to cool and harden at ambient air.

Eve Irritation Test

The clear cleansing bar prepared in Example 1 was tested by a Transepithelial Permeability Assay (TEP) to measure eye irritation potential. TEP is a mechanistic assay, which measures the damage to a layer of epithelial cells. Exposure of a layer of Madin-Darby Canine Kidney Epithelial (MDCK) cells, grown on a microporous membrane, to a test sample is a model of the first event that occurs when an irritant comes in contact with the eyes. In vivo, the outermost layers of the corneal epithelium form a selectively permeable barrier due to the tight junctions between the cells. On exposure to an irritant, the tight junctions separate removing the permeability barrier. Fluid is imbibed to the underlying layers of epithelium and to the stroma, causing the collagen lamellae to separate, and resulting in opacity. Damage is measured spectrophotometrically, by measuring the amount of marker dye that leaks through the cell layer and microporous membrane to the lower well. A TEP score of 2.2% or higher is considered a pass, a score of 1.78% to 2.19% is considered borderline, and a score of 1.79% or below is considered a fail. The procedure was in accordance with the TEP test, as set forth in Invittox Protocol Number 86 (May 1994). The results of the test are reported in Table 1.

TABLE 1

| Sample | Mean $EC_{50}$ + δn-1 | Rating |
|---|---|---|
| Example 1 | 32.97 +/− 11.83 | Pass |

The clear cleansing bar of this invention was found to be non-irritating to the eyes.

Cleansing Bar Clarity

The clarity of the cleansing bar was assessed visually by a trained expert evaluator using a scale ranking from 1—totally clear to 10 —totally opaque. Example 1 had a mean ranking of 3.5.

Cleansing Bar Mush

A test was performed on the sample from Example I to determine how much mush forms. Water (40 mL at 25° C. and 4 gpg hardness) was poured at the bottom of a 16 mm ×90 mm petri dish. After taking its initial weight, the bar was placed on top of the water-filled dish. A triangular rod was used to support the bar and keep it in contact with the water. The bar was left to stand for 16 hours after which the mush or gel that formed on the side of the bar in contact with water was scrapped using a spatula. The bar was then allowed to dry at ambient temperature for 4 hours. The final weight was taken after drying. The percent bar mush was then calculated as:

$$\frac{\text{Initial Weight of Bar} - \text{Final Weight of Bar}}{\text{Initial Weight of Bar}} \times 100\%$$

The results of the test are shown in Table 2.

TABLE 2

| Sample | % Bar Mush |
|---|---|
| Example 1 | 4.5 +/− 0.5 |

The cleansing bar from Example 1 was shown to form very little mush.

The cleansing bar from Example 1 was shown to form very little mush.

Bar Wear and Foaming

The sample from Example 1 was also tested for bar wear and foam volume using a tumbling tube apparatus. The tumbling tube apparatus was equipped with six 1000 mL cylinders and mounted on a rotating casing with variable speed and number of rotations. In this test, each cylinder was filled with 500 mL of water.

Bars were cut into approximately $2\times2\times mm^3$, each weighing approximately 5g. Test bars were added into each of the cylinders. The cylinders were rotated at 100 rpm for 50 revolutions. The foam volume was then read using the graduations of the cylinder. Bars were removed from the cylinders and allowed to dry at ambient temperature for 4 hours. The final weight of each bar was recorded. The percent bar wear was calculated as:

$$\frac{\text{Initial Weight of Bar} - \text{Final Weight of Bar}}{\text{Initial Weight of Bar}} \times 100\%$$

The results of the tests are shown in Table 3.

TABLE 3

| Sample | % Bar Wear | Foam |
|---|---|---|
| Example 1 | 13.2 +/− 0.5 | 292 mL +/− 1.0 |
| Comparative | 57.6 +/− 0.6 | 6.7 +/− 0.7 |

The comparative sample was Johnson's Baby Clear Soap. The cleansing bar of Example 1 was shown to have good foaming and bar wear properties.

Example 2

A second sample was prepared following the method of Example 1, but a different surfactant combination was utilized. The surfactant combination was as follows:

| | |
|---|---|
| sodium laureth sulfate | 100.0 g |
| POE sorbitan laurate | 50.0 g |
| cocamidopropylbetaine | 80.0 g |
| lauric-myristic phosphobetaine | 20.0 g |

Example 3

A third sample was prepared following the method of Example 1, but a different surfactant combination was utilized. The surfactant combination was as

| | |
|---|---|
| sodium laureth sulfate | 127.3 g |
| lauroamphoglycinate | 46.3 g |
| lauryl betaine | 33.3 g |

The foam volume and percent bar wear of examples 2 and 3 are shown in Table 4.

TABLE 4

| Sample | % Bar Wear | Foam |
|---|---|---|
| Example 2 | 17.0 | 290 mL |
| Example 3 | 18.6 | 540 mL |

Both Examples 2 and 3 had good foaming and bar wear properties.

Example 4

A fourth sample was prepared following the method of Example 1, but solidifying synergists were added to the composition. The solidifying synergists were hydroxypropyl cellulose (10 g) and hydroxypropyl guar (10 g).

Example 5

An opaque bar composition was prepared following the method of Example 1, but using sodium cocoyl isethionate as a surfactant. The cleansing bar composition was as follows:

| Ingredient | Weight (grams) |
|---|---|
| propylene glycol | 518.0 |
| hydroxypropyl cellulose | 12.0 |

-continued

| Ingredient | Weight (grams) |
|---|---|
| dibenzylidene sorbitol | 2.7 |
| sodium cocoylisethionate | 12.5 |
| glycerin | 27.2 |

Example 6

A sixth sample was prepared following the method of Example 1, but without hydroxypropyl cellulose in the formulation. TEP results are summarized in Table 5.

Example 7

A seventh sample was prepared following the method of Example 1, with addition of the following ingredients: PPG-Hydroxyethyl Caprylamide at 2%, Fragrance at 0.20%, and FD&C Red # 40 colorant. TEP, foam volume and bar wear rate results are summarized in Table 5.

TABLE 5

| Sample | % Bar Wear | Foam | Mean $EC_{50}$ + δn-1 |
|---|---|---|---|
| Example 6 | Not tested | Not tested | 38.29 |
| Example 7 | 23.9 | 292.5 mL | 32.85 |

Examples 6 and 7 were shown to be non-irritating to the eyes. Example 7 had good bar wear and foaming properties.

What is claimed:

1. A clear cleansing bar composition comprising:

a) from about 0.5% to about 30% of at least one amphoteric surfactant;

b) from about 0.5% to about 30% of at least one anionic surfactant;

c) from about 0.5% to about 30% of at least one non-ionic surfactant; and from about 0.1% to about 20% of a solidifying agent selected from the group consisting of dibenzylidene sorbitol, dibenzylidenexylitol, dibenzylidene ribitol, and mixtures thereof; and d) from about 10% to about 90% of at least one organic solvent;

wherein the composition is not irritating to the eyes.

2. The clear cleansing bar composition of claim 1, wherein the at least one organic solvent is selected from the group consisting of dihydroxy aliphatic alcohols containing from 3 to 6 carbon atoms; monohydric alcohols; polyhydric alcohols; and mixtures thereof.

3. The clear cleansing bar composition of claim 2, wherein the at least one organic solvent is selected from the group consisting of glycerin, propylene glycol, polyethylene glycol, polypropylene glycol, and mixtures thereof.

4. The clear cleansing bar composition of claim 1, wherein the at least one organic solvent is selected from the group consisting of dihydroxy aliphatic alcohols containing from 3 to 6 carbon atoms; monohydric alcohols; polyhydric alcohols; and mixtures thereof.

5. The clear cleansing bar composition of claim 2, wherein the at least one organic solvent is selected from the group consisting of glycerin, propylene glycol, polyethylene glycol, polyethylene glycol, and mixtures thereof.

6. The clear cleansing bar composition of claim 1, wherein the at least one amphoteric surfactant is selected form the group consisting of amphocarboxylates, alkyl betaines, amidoalkyl betaines, amidoalkyl sultaines, amphophosphates, phosphobetaines, pyrophosphobetaines, carboxyalkyl alkyl polyamines, and mixtures thereof.

7. The clear cleansing bar composition of claim 4, wherein the at least one amphoteric surfactant is selected form the group consisting of cocamidopropylbetaine, lauroamphoglycinate, lauric-myristicphosphobetaines, and lauryl betaine.

8. The clear cleansing bar composition of claim 1, wherein the at least one anionic surfactant is selected form the group consisting of alkyl sulfates; alkyl ether sulfates; alkyl monoglyceryl ether sulfates; alkyl monoglyceride sulfates; alkyl monoglyceride sulfonates; alkyl sulfonates; alkylaryl sulfonates; alkyl sulfosuccinates; alkyl ether sulfosuccinates; alkyl sulfosuccinamates; alkyl amidosulfosuccinates; alkyl carboxylates; alkyl amidoethercarboxylates;alkyl succinates; fatty acyl sarcosinates; fatty acyl amino acids; fatty acyl taurates; fatty alkyl sulfoacetates; alkyl phosphates; and mixtures thereof, wherein the alkyl group has from about 10 to about 16 carbon atoms.

9. The clear cleansing bar composition of claim, 7, wherein the at least one anionic surfactant is selected form the group consisting of sodium laureth sulfate and sodium laureth- 13 carboxylates.

10. The clear cleansing bar composition of claim 1, wherein the at least one nonionic surfactant is selected form the group consisting of polyoxyethylene derivatives of polyol esters, wherein the polyoxyethylene derivative of polyol ester (1) is derived from (a) a fatty acid containing from about 8 to about 22 carbon atoms, and (b) a polyol selected from sorbitol, sorbitan, glucose,α-methyl glucoside, polyglucose having an average of about 1 to about 3 glucose residues per molecule, glycerin, pentaerythritol and mixtures thereof, (2) contains an average of from about 10 to about 120, oxyethylene units; and (3) has an average of about 1 to about 3 fatty acid residues per mole of polyoxyethylene derivative of polyol ester; long chain alkyl glucosides, and polyglucosides, which are the condensation products of (a) a long chain alcohol containing from about 6 to about 22 carbon atoms, with (b) glucose or a glucose-containing polymer.

11. The clear cleansing bar composition of claim 10, further comprising:

f) from about 0.05% to about 10% of a solidifying synergist.

12. The clear cleansing bar composition of claim 11, wherein the solidifying synergist is selected from the group consisting of cellulose and guar derivatives, acrylic acid polymers, polyacrylamides, alkylene/alkylene oxide polymers, smectite hydrophilic and organoclays, hydrated and fumed silicas, gelatin, keratin, xanthan and guar gums, carrageenan, agar and alginates.

* * * * *